United States Patent
Spahn

(10) Patent No.: US 7,120,231 B2
(45) Date of Patent: Oct. 10, 2006

(54) X-RAY SYSTEM WITH A BEAM-GATING DIAPHRAGM, AND METHOD FOR AUTOMATIC ADJUSTMENT THEREOF

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/841,339

(22) Filed: May 7, 2004

(65) Prior Publication Data

US 2004/0264646 A1 Dec. 30, 2004

(30) Foreign Application Priority Data

May 9, 2003 (DE) ................ 103 20 862

(51) Int. Cl.
*G21K 5/04* (2006.01)
(52) U.S. Cl. ................ 378/151; 378/98.12; 250/515.1
(58) Field of Classification Search ................ 378/151; 250/515.1
See application file for complete search history.

(56) References Cited

U.S. PATENT DOCUMENTS

| 4,672,652 | A | | 6/1987 | Hüttenrauch et al. | |
| 4,817,125 | A | * | 3/1989 | Sklebitz | 378/152 |
| 6,055,295 | A | * | 4/2000 | Murthy et al. | 378/151 |
| 6,106,152 | A | * | 8/2000 | Thunberg | 378/205 |
| 6,222,906 | B1 | * | 4/2001 | Sakaguchi et al. | 378/98.8 |
| 6,459,765 | B1 | * | 10/2002 | Ganin et al. | 378/108 |
| 6,600,810 | B1 | * | 7/2003 | Hughes | 378/152 |
| 6,795,526 | B1 | * | 9/2004 | Kump et al. | 378/116 |
| 6,800,858 | B1 | * | 10/2004 | Seppi | 250/370.11 |
| 2004/0096033 | A1 | * | 5/2004 | Seppi et al. | 378/65 |
| 2004/0202281 | A1 | * | 10/2004 | Colbeth et al. | 378/98.8 |
| 2004/0240621 | A1 | * | 12/2004 | Noguchi | 378/150 |

* cited by examiner

*Primary Examiner*—Edward J. Glick
*Assistant Examiner*—Krystyna Suchecki
(74) *Attorney, Agent, or Firm*—Schiff Hardin LLP

(57) ABSTRACT

In a method for automatic adjustment of a diaphragm in an x-ray system, the diaphragm having a number of adjustable diaphragm elements for a subsequent x-ray exposure of an examination subject, the individual diaphragm elements are respectively positioned such that, considered in a projection lying in a detector plane, abut the contours of the acquisition subject or are situated at a small distance therefrom for this positioning, first a subject localization exposure is generated with a low radiation dose with an open diaphragm. This subject localization exposure is analyzed to determine contours of the exposure subject. The positions of the diaphragm elements are calculated using the determined contours, and then the diaphragm elements are moved into the calculated positions.

12 Claims, 3 Drawing Sheets

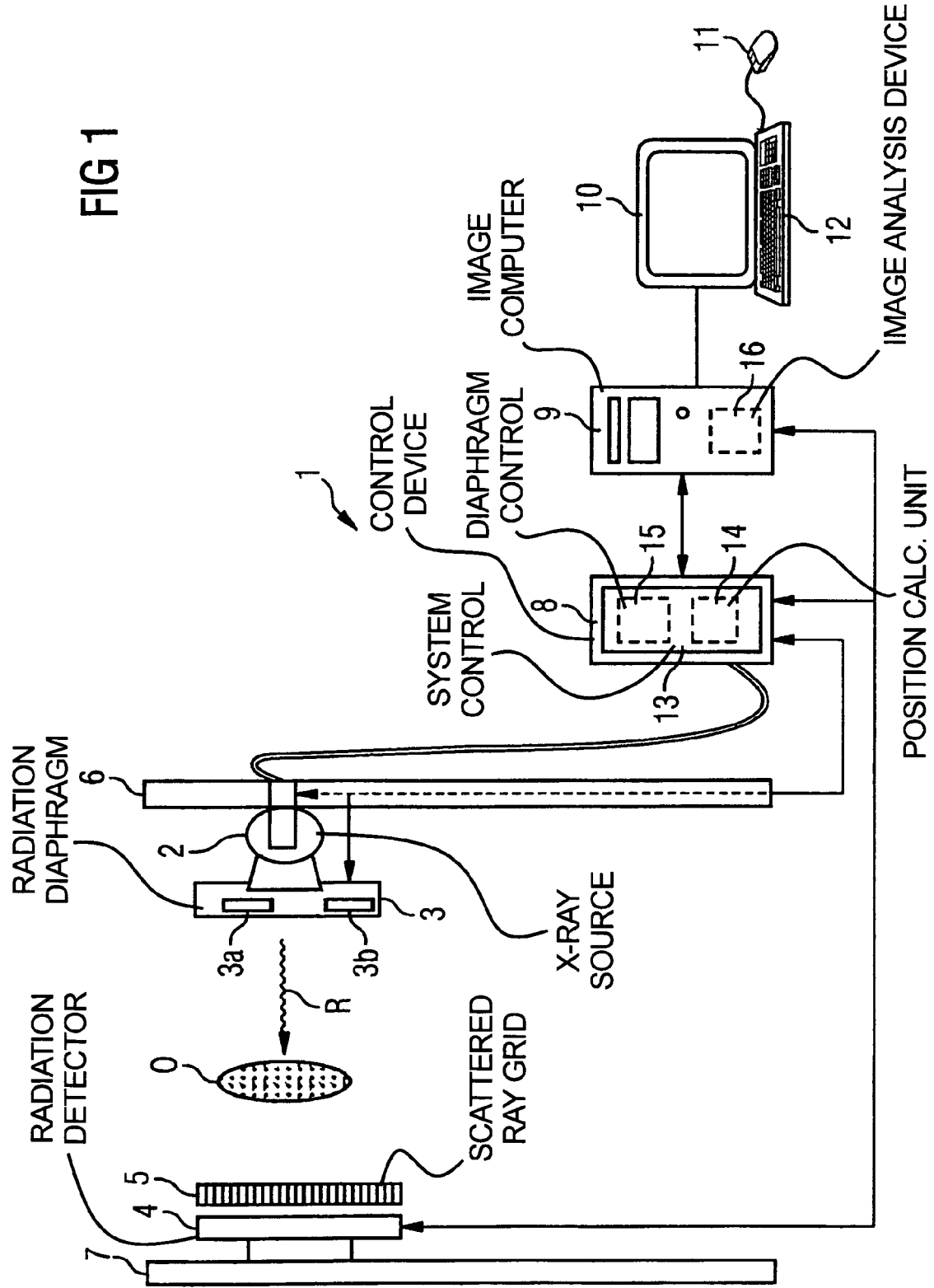

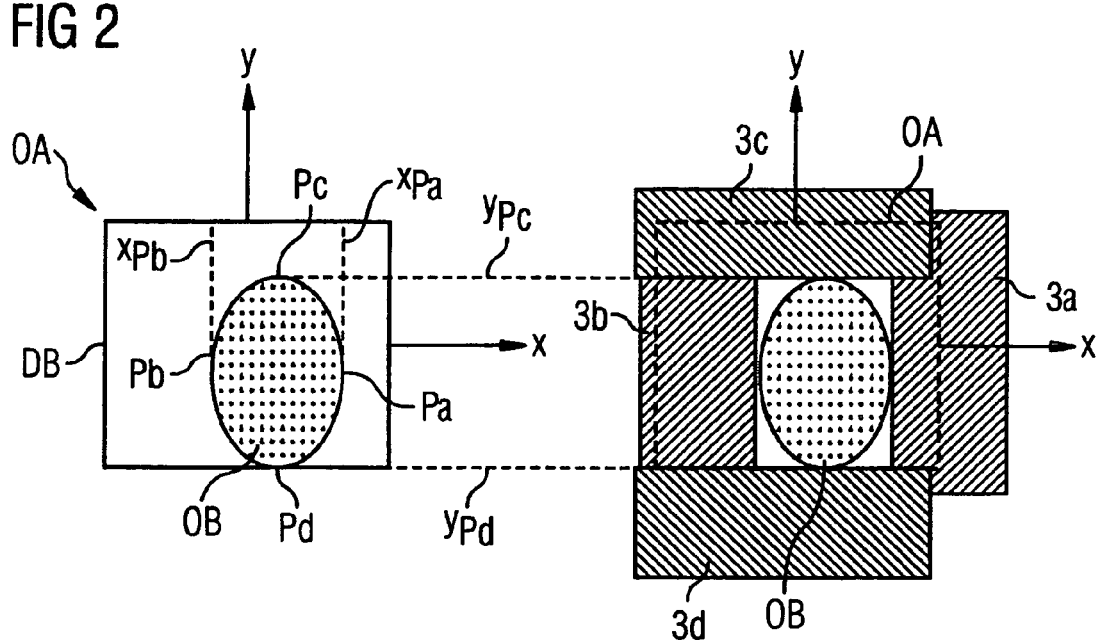
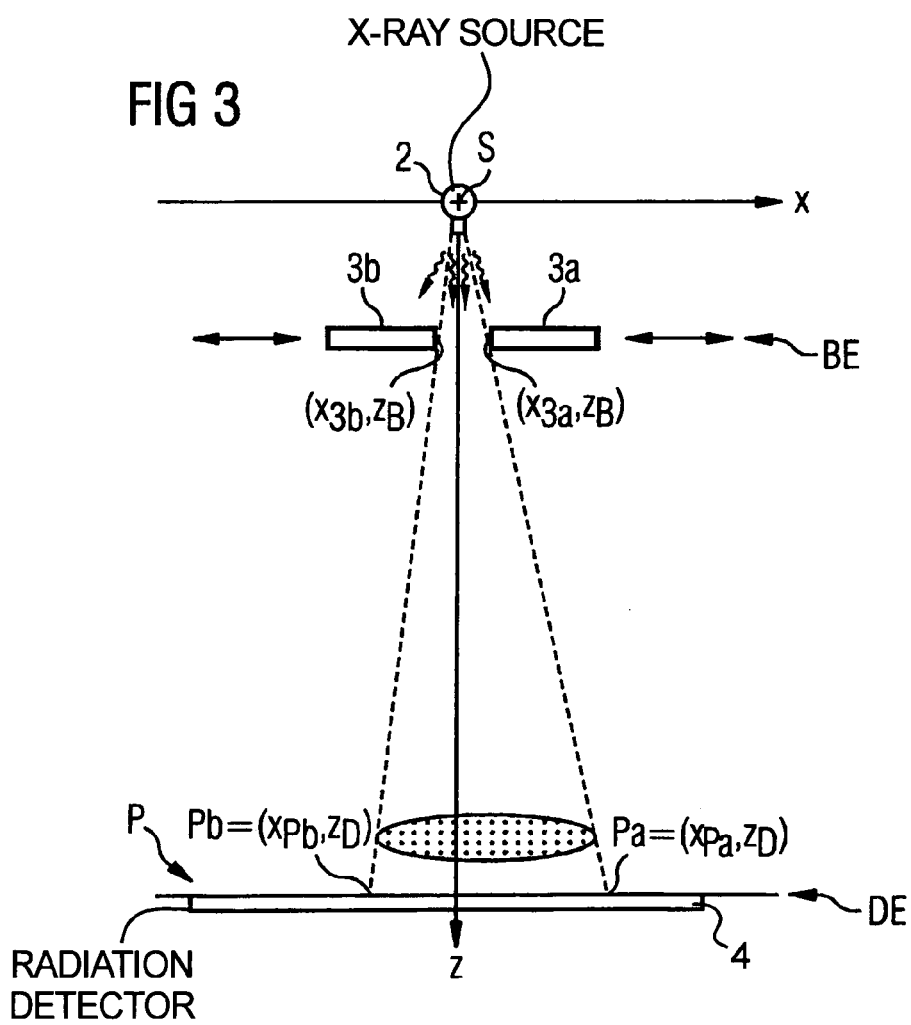

X-RAY SYSTEM WITH A BEAM-GATING DIAPHRAGM, AND METHOD FOR AUTOMATIC ADJUSTMENT THEREOF

BACKGROUND OF THE INVENTION

1. Field of the Invention

The present invention concerns a method for automatically adjusting a radiation-gating diaphragm (having a number of adjustable diaphragm elements) for a subsequent x-ray exposure of an examination subject, wherein the individual diaphragm elements are respectively positioned such that they—considered in a projection lying in a detector plane—contact the contours of the acquisition subject or are arranged at a small distance therefrom. The invention also concerns an x-ray system with an x-ray source, an x-ray detector, a diaphragm (arranged in an x-ray beam path between the x-ray source and the x-ray detector) with a number of automatically adjustable diaphragm elements, and a diaphragm control device in order to position the individual diaphragm elements.

2. Description of the Prior Art

A diaphragm of the above type, known as a "depth diaphragm" or a "primary beam diaphragm" normally is located in the beam path between the x-ray source and the acquisition subject. It primarily has the object to allow only the acquisition subject to be irradiated, and not the surrounding areas. For example, in exposures of specific body parts or organs of a person, only tissue is irradiated that is necessary for the diagnosis or the planned intervention, such that the radiation dose for the subject is reduced. Moreover, given exposures in which, for example, the subject is a body part of a person, x-ray radiation is prevented from arriving unattenuated directly from the x-ray source (past the subject) to the detector. Such "direct radiation" can lead to image artifacts depending on the design of the detector. Thus, for example, due to scattering or due to transverse re-direction of the radiation in the detector glass, a lateral spatial expansion of the signal in the subject region can occur. This phenomenon can lead in an image intensifier to a phenomenon known as "low frequency drop". Moreover, such direct radiation can lead to the individual structural elements of a planar image detector, assembled from a number of detector parts, respectively becoming visible at the Impact locations and interfering in the image. By the use of the depth diaphragm that covers (blocks) the irrelevant regions, so the beam precision is increased, and the image quality is improved.

Such a diaphragm can either completely gate the x-ray radiation or can be semi-transparent and attenuate the radiation. The first type of diaphragm has the advantage that no x-ray radiation whatsoever arrives in the irrelevant region. By contrast, the second type of diaphragm has the advantage that, although the regions located near the actual exposure subject will appear lighter in the image, to the same extent that the visibility is increased in the region of interest, but high-contrast objects (such as, for example, operating instruments) that are laterally introduced into the examination subject) are still visible. In both versions, an optimally good adaptation of the diaphragm to the respective examination subject is important for the proper functioning of such a diaphragm, so that the examination subject is not covered by the diaphragm plates, and the surrounding regions of no interest are covered to the extent possible.

In most conventional x-ray examination apparatuses, it is only possible to effect the adjustment of the diaphragm by hand, for example with the aid of a light-beam localizer. Moreover, there are x-ray systems in which it is possible to implement an automatic preadjustment using an organ program downloaded into a system control that before any manual adjustment, an approximate diaphragm adjustment to the region of interest is made. A disadvantage is that the actual position of the examination subject can vary significantly due to the positioning (for example of a patient) and variation in the size of a patient or of the respective examination subject. An ideal adjustment thus is not possible with these methods. In contrast to this, an exact adjustment of the depth diaphragm by fine adjustment by hand requires a relatively long time, which is counter to achieving an optimal workflow with short wait times for the patients.

German 35 00 812 describes an x-ray irradiation apparatus with a diaphragm of the above-described type, which has a number of diaphragm elements in the form of plates or lamellae that are positioned such that they abut the contours of the examination subject—viewed as a projection in the detector plane—at least at one point, meaning that the diaphragm elements projected from the x-ray source onto the detector plane abut the contours of the examination subject likewise projected from the x-ray source onto the detector plane. For this purpose, the apparatus has a placement device for the individual plates. The detector an x-ray image intensifier with a television camera connected thereto to generate video signals. Connected to the television camera is a special evaluation circuit which is designed such that specific image regions in the video signal are each associated with specific plates or lamellae. At the beginning of an exposure of an examination subject, the diaphragm is completely open. With the control signals acquired from the video signal, the individual plates are then controlled by the evaluation circuit such that they move toward one another and thus slowly close the diaphragm. Each individual plate is stopped as to its closing motion when a specific preselected brightness level is undershot in the portion of the video signal associated with the corresponding plate. This technique consequently requires that the subject be irradiated for a certain amount of time during the adjustment of the diaphragm. Moreover, the use of the technique is limited to x-ray detectors with a video camera and with a special evaluation circuit for the video signals.

SUMMARY OF THE INVENTION

An object of the present invention is to provide a method for automatic adjustment of a diaphragm and a corresponding x-ray system with such a diaphragm which enable an optimally simple, fast and good adjustment of the diaphragm before an x-ray acquisition.

The object is achieved in accordance with the invention by a method and apparatus wherein, to position the individual diaphragm elements, a subject localization exposure is initially generated with low dosage with an open diaphragm. This subject localization exposure is analyzed to determine a contour of the exposure subject and, using the determined contours, the positions of the diaphragm elements are then calculated and the diaphragm elements are moved into the calculated positions so as to substantially abut the contour projected into the detector plane. (As used herein, "substantially abut" encompasses precise abutment with the contour projected into the detector plane, as well as a position a short distance away from precise abutment.) The subject localization exposure is implemented in an optimally short timeframe before the actual exposure, which preferably is not longer than the time necessary for a complete calculation and adjustment of the positions of the diaphragm elements. The dose thus can be very significantly less than in the actual exposure, for example only a tenth or a hundredth of the "normal" dose.

To implement this method, in addition to the previously cited components, the inventive x-ray system has an x-ray system control that causes the subject localization exposure to be generated before an x-ray exposure with a low dose and with an open diaphragm; an image analysis device that analyzes the subject localization exposure to determine the contours of the exposure subject; and a position calculation device that, using the determined contours, calculates the positions of the diaphragm elements and conveys signals representing the calculated positions to the diaphragm control device for positioning the diaphragm elements.

The invention has the advantage that a single short x-ray exposure (called a "pre-shot" below) with a very low dose is sufficient to determine the diaphragm position. This means that the additional dose exposure for the patient for the adjustment of the diaphragm positions is low. Moreover, in principle this method can be used in every type of x-ray apparatus that has a diaphragm control device for automatic positioning of the individual diaphragm elements. In particular an existing x-ray system control can be retrofitted without difficulty by reprogramming, for example with a corresponding software module. The image analysis device and the position calculation units likewise can be implemented in the form of suitable software modules in a central processor of the x-ray apparatus, for example of the x-ray system control itself or an image processing device that is already present. An existing x-ray apparatus thus can be inventively retrofitted at any time.

In a preferred exemplary embodiment, for the generation of the subject localization exposure a number of adjacent image pixels are combined in groups to form a common image point. The resolution is reduced by the combinations (for example by a common readout) of individual pixels into groups of, for example, 2×2, 3×3 or 10×10 pixels, and thus the size of the image matrix is reduced. The calculation time is thereby reduced and the signal-to-noise ratio in the subject localization exposure, acquired with only a low dose is improved.

Furthermore, the subject localization exposure can be added pixel-by-pixel to a subsequently obtained x-ray exposure. This means that the pre-shot and the actual exposure are added by calculation technologies, such that the dose used for the pre-shot is also completely utilized for generating the diagnostic image. Due to the very short time span between the pre-shot and the actual exposure, possible image artifacts are largely reduced and are therefore negligible.

In the analysis of subject localization exposure, it is advisable to use known techniques in the image processing of x-ray images. One such method is direct ray detection, which is already used today in many cases for automatic windowing in the framework of the image processing. The subject localization exposure can be converted by means of the direct ray detection method into a representation in which the direct radiation region in which the x-ray radiation directly strikes unattenuated on the detector, is shown with a specific value, for example with 0, and the subject region is itself coded with another value, for example with 1. The result is then a binary image which can be very simply processed.

There are a number of possibilities for precise calculation of the optimal positions of the diaphragm elements using the subject localization exposure.

In a preferred version, the position of each diaphragm elements is calculated using the following position data:
the coordinates of at least one point on the contour of the exposure subject in the subject localization exposure (that corresponds to the contour of the examination subject projected from the x-ray source on the detector plane);
the position of the detector plane in which the image is acquired, relative to a primary x-ray beam direction (meaning the position along the direct connecting line between the x-ray source and the x-ray detector);
the position of the diaphragm plane in which the diaphragm elements are adjustably arranged, relative to the primary x-ray beam direction.

In most cases, the diaphragm plane and the detector plane are at right angles to the primary x-ray beam direction. The specification of a coordinate, for example for the distance of the diaphragm plane and detector plane relative to an x-ray source, or to a focal spot of the x-ray source, is sufficient to completely specify the positions of the detector plane and the diaphragm plane. When the detector plane and/or the diaphragm plane is slanted relative to the primary x-ray beam direction, the position must be specified by the specification of further coordinates, for example the coordinates of three points on the plane or specific angle specifications. Insofar as the distances of the diaphragm and the detector from the x-ray source remain the same, the coordinates of these positions are fixed anyway and no longer need to be-actively determined or calculated for the diagnostic exposure.

To calculate the desired position of a diaphragm element, the coordinates of such a point which—considered in a projection in the detector plane—form an outermost point of the contour in the direction of the appertaining diaphragm element are preferably used on the contour of the exposure subject in the subject localization exposure. This means the points on the contour are precisely considered that first abut the diaphragm elements or would first be covered by these diaphragm elements given a movement of the diaphragm elements in a closing direction (considered in the projection on the detector plane).

By suitable selection of a coordinate system in which the position data are determined and the calculations implemented, the necessary times for the determination of the positions of the diaphragm elements can be optimized.

When the detector has a detector surface with detector elements in a matrix (meaning when it is, for example, a solid state detector with an active readout matrix) and the detector surface is situated perpendicularly to the primary x-ray beam direction, is appropriate to a coordinate system having an origin at the focal spot of the x-ray source and having coordinate axes in the primary x-ray beam direction (the z-axis in the following) and parallel to the rows and columns of the detector surface (x- and y-axes). The coordinates of a point on the contour of the exposure subject correspond in this coordinate system to the row and column numbers of the respective image pixel, meaning of the appertaining matrix element.

In such a coordinate system, the coordinates of the boundary position (lying in the closing direction) of a diaphragm element within the diaphragm plane can be determined in a very simple manner by means of a ray set calculation. For example, the coordinates of the point on the contour of the exposure subject at which the appertaining diaphragm element (considered in the projection lying in the detector plane) would first contact the contour of the exposure subject given an adjustment in the closing direction, can be derived directly from the subject localization exposure. These coordinates then must only be multiplied with the quotients from the z-coordinate of the position of the diaphragm plane and the z-coordinate of the position of the detector plane in order to obtain the coordinates of the desired point in the image plane over which the appertaining diaphragm element may not be moved in the closing direction without covering the exposure subject.

The inventive x-ray system in principle can have an arbitrarily designed diaphragms with variously arranged individual diaphragm elements. Preferably, the diaphragm allows asymmetric adjustment with regard to a diaphragm center point. In a preferred exemplary embodiment, however, the diaphragm is designed such that the diaphragm elements can be radially moved forward and backward in the direction of the diaphragm center point at different angles, meaning from various directions. Each diaphragm element has an inner edge proceeding toward the diaphragm center point and perpendicular to the movement direction. Such a diaphragm can have 4, 6, 8 or more individual elements. Depending on the number of elements, the diaphragm can be designed rectangular, hexagonal, octagonal etc. with regard to its inner contours. The diaphragm elements, however, in principle can exhibit any other arbitrary shape.

DESCRIPTION OF THE DRAWINGS

FIG. 1 is a schematic illustration of an x-ray system with an inventive diaphragm.

FIG. 2 schematically shows the exposure subject projected from the x-ray source on the detector plane, without a diaphragm (left side) and with a closed diaphragm with diaphragm elements bordering on the contour of the exposure subject to cover the direct radiation region (right side).

FIG. 3 shows the geometric arrangement of the x-ray source, the inventive diaphragm, the exposure subject and the detector in the primary x-ray beam direction.

DESCRIPTION OF THE PREFERRED EMBODIMENTS

Figure 4:
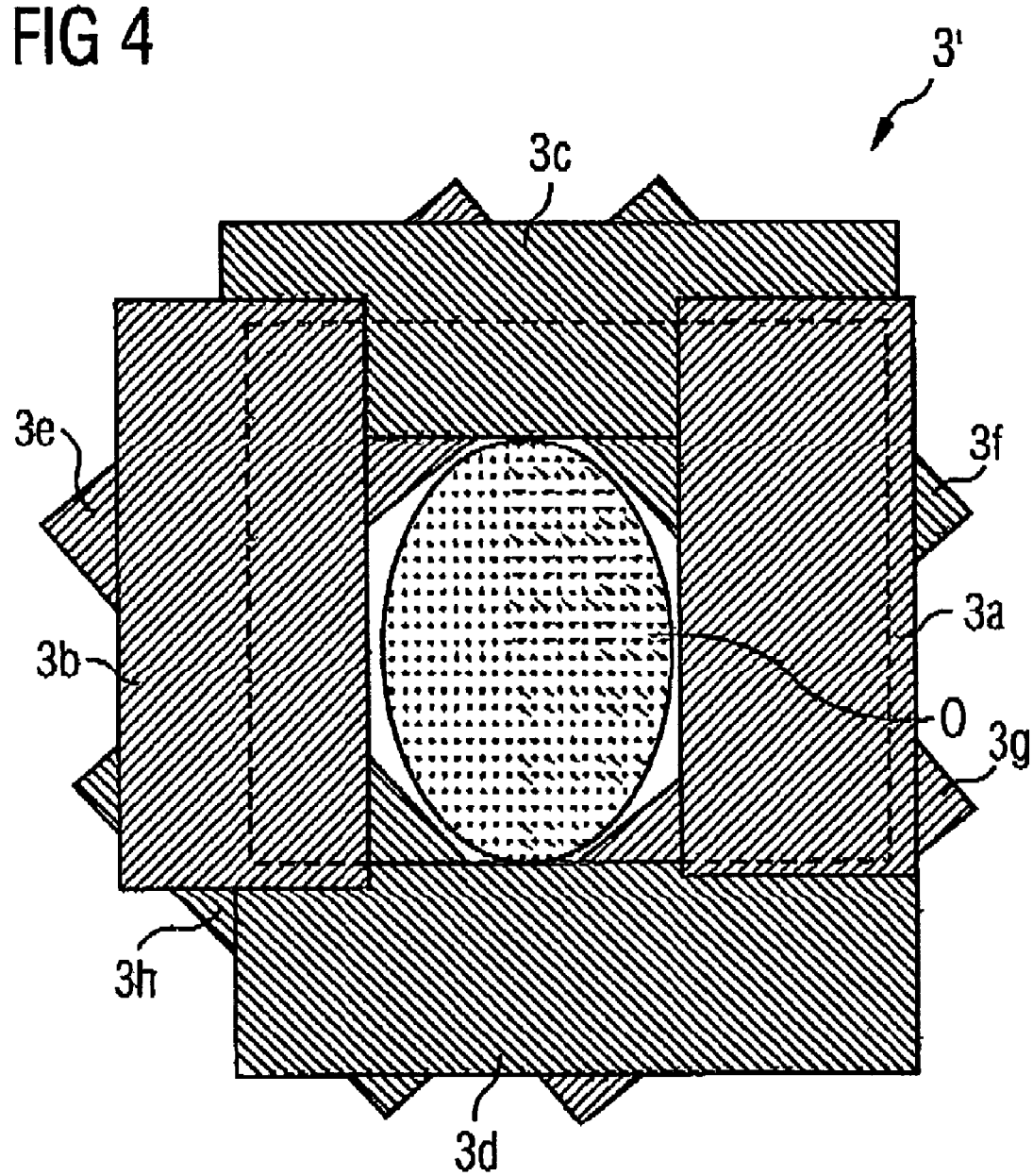
FIG. 4 schematically shows an inventive diaphragm with eight individual diaphragm elements.

The x-ray system 1 shown in FIG. 1 has a height-adjustable x-ray source 2 mounted on an emitter stand 6 with a depth diaphragm 3 mounted directly in front of it, which is constructed and operable according to the invention. A digital x-ray detector 4 with a scattered-ray grid 5 in front of it is height-adjustably mounted on the image acquisition side to a receiver stand 7. To generate an x-ray exposure of a subject O, the subject O is positioned in the beam path between the depth diaphragm 3 and the scattered-ray grid 5.

The x-ray radiator 2, the depth diaphragm 3 and the digital detector 4 are respectively connected via control lines, data lines and/or supply lines with a control device 8 which contains an x-ray voltage generator and a system control 13, with which image acquisition using the individual components 2, 3, 4 is controlled. Components of the system control 13 are a position calculation unit 14 in order to calculate the positions of the individual diaphragm elements 3a, 3b of the depth diaphragm 3 and a diaphragm control 15 which controls the individual diaphragm elements 3a, 3b or actuators therefor (such as, for example, step motors) to adjust the diaphragm elements 3a, 3b associated with the diaphragm elements 3a, 3b.

Moreover, connected to the system control 13 is an image computer 9 in which, among other things, an image analysis device 16 is implemented. The image computer 9 is connected via a data line with the digital detector 4 in order to read out the data generated thereby and to generate the desired x-ray images. These x-ray images can then be displayed on a connected supervision monitor 10. Operation of the image computer 9 and the control device 8, in particular of the system control 13, is possible with the aid of the supervision monitor 10 as well as appropriate user interfaces, here a mouse 11 and a keyboard 12.

In addition to the shown components, the x-ray system 1 also can have further components that are typically present in or at such x-ray systems, such as, for example, an interface to connect to a computer network, in particular a radiological information system (RIS) and/or an image archiving and communication system (PACS). Such further components however, are not shown for clarity.

A method for correctly setting the diaphragm elements according to the invention in an x-ray system 1 according to FIG. 1 is explained in the following, using FIGS. 2 and 3.

First, immediately before the actual x-ray exposure, initiated by the system control 13, a subject localization exposure OA is acquired with the detector 4 in advance with a very low dose (for example a hundredth of the dose used for the actual x-ray exposure) given a wide-open depth diaphragm 3. The acquisition of this "pre-shot" ensues approximately one second or less before the actual x-ray exposure. The digital detector 4 is read out at this time and the data are transmitted to the image computer 9, where the data are processed in an image analysis device 16. A direct radiation detection is implemented next, which separates the sites of the direct radiation on which the x-ray radiation strikes unattenuated on the detector 4 from the points of the subject region. The result of the calculation is a binary representation of the subject localization exposure, in which the image points of the subject region are coded with 1 and the image points of the direct radiation region are coded with 0. Such a binary subject localization exposure OA is schematically shown in the left half of the FIG. 2. The direct radiation region DB and the subject region OB are clearly distinct from one another in such a binary representation, such that in particular the contours K of the examination subject O can be easily recognized. As can be seen from FIG. 3, the subject localization exposure OA is a projection P of the examination subject O imaged from the x-ray source 2 on the detector plane DE.

For the further calculations, for simplicity the following assumptions are made in the exemplary embodiment:

a) All calculations occur in a coordinate system having an origin S at the focal spot of the x-ray source 2.

b) The diaphragm plane BE in which the individual diaphragm elements 3a, 3b can be moved toward one another to close the diaphragm 3 and the detector plane DE lie exactly at right angles to the primary x-ray beam direction R, meaning at right angles to the direct connecting line between the x-ray source 2 and the detector 4. This direction is in the following the z-axis of the coordinate system.

c) The other two coordinate axes x and y are perpendicular to this z-axis, and are oriented corresponding to the rows and columns of the active matrix of the digital detector 4.

d) The diaphragm 3 has four individual diaphragm elements (3a, 3b, 3c, 3d) that can be moved toward one another from the right, from the left, from below and from above, these movement directions proceeding along the coordinate axes x and y (see FIG. 2).

Although these assumptions significantly simplify the calculations, they are not absolutely necessary. Insofar as other forms of diaphragms or other geometric arrangements (such as, for example, an angular irradiation or the x-ray radiation or rotation of the x-ray source and/or of the detector plane and/or of the diaphragm plane) are provided, correspondingly more position data must be considered and incorporated into the calculation. If necessary, in such cases the selection of another coordinate system can be useful.

With the aid of the subject localization exposure OA, the subject borders are first determined in order to establish how far the individual diaphragm elements 3a, 3b, 3c, 3d move in the direction of the exposure subject O, meaning how far they can be moved toward one another without overlapping the electrically-conductive structure O in the projection P. This depends on, among other things, the geometric arrangement and shape of the individual diaphragm elements 3a, 3b, 3c, 3d.

It is normally reasonable to first determine the points Pa, Pb, Pc, Pd on the contour K of the exposure subject O which, in the subject localization exposure OA, form an outermost point of the contour K in the direction of the respective diaphragm element 3a, 3b, 3c, 3d. In the present case, this means the point Pa farthest to the right, the point Pb farthest to the left, the uppermost point Pc and the lowermost point Pd of the contour K are sought. Insofar as the individual diaphragm elements 3a, 3b, 3c, 3d are moved together to the extent that they respectively—viewed in the projection P—contact these points Pa, Pb, Pc, Pd, the direct radiation region DB is gated as much as possible without the diaphragm 3 covering the subject O itself (see FIG. 2, right side). In the selected geometric arrangement, the coordinates of these points Pa, Pb, Pc, Pd are relatively simple to determine, in particular when the subject localization exposure OA has already been converted into the binary representation in which the subject region is coded with 1 and the direct radiation region is coded with 0. For this purpose, only the image pixels coded with 1 whose "coordinates" in the image matrix exhibit the largest and the smallest x-value or, respectively, the largest and the smallest y-value are to be sought. This can be implemented extraordinarily quickly and simply by calculation techniques.

It is then only necessary to calculate these "boundary coordinates" (up to which an inward adjustment of the diaphragm elements 3a, 3b, 3c, 3d is possible without overlapping the subject O) found in the detector plane DE in the projection P back to the diaphragm plane BE. This is shown in FIG. 3 using the diaphragm elements 3a, 3b. Since both diaphragm elements 3a, 3b in the exemplary embodiment are arranged such that they can only be moved inward or outward in the direction of the x-coordinate, only the x-coordinate is significant within the detector plane DE or the diaphragm plane BE. Further significant coordinates are the distance $z_D$ (fixed in advance anyway) of detector plane DE and the distance $z_B$ of the diaphragm 3 from the origin S of the coordinate system, meaning from the focal spot of the x-ray source 2.

Using a simple beam set calculation, the coordinate $x_{3a}$ of the "boundary position" (up to which the inner edge of the diaphragm element 3a can be moved inward without covering the subject O) can be calculated according to the formula $$x_{3a} = x_{3b} \cdot \frac{z_B}{z_D}$$

from the x-coordinate $X_{Pa}$ of the found boundary point Pa on the contour K of the exposure subject O projected on the detector plane DE. In the same manner, the coordinate $x_{3b}$ of the "boundary position" for the opposite diaphragm element 3b is obtained from the coordinate $x_{Pb}$ of the point Pb in the subject localization exposure OA. A calculation for the upper and lower diaphragm elements 3c, 3d can likewise ensue, for which the y-coordinates are used.

After the coordinates $x_{3a}$, $x_{3b}$ (or $y_{3c}$, $y_{3d}$) of the boundary positions have been calculated, these are transferred to the diaphragm control 15, which controls the motorized actuation (not shown) of the individual diaphragm elements 3a, 3b, 3c, 3d such that the diaphragm elements 3a, 3b, 3c, 3d are to be moved toward one another until the inner edges of the diaphragm elements 3a, 3b, 3c, 3d arrive directly on the calculated boundary coordinates $x_{3a}$, $x_{3b}$, $y_{3c}$, $y_{3d}$. Alternatively, the adjustment can ensue such that the inner edges lie at a predetermined small distance outside of the calculation boundary coordinates.

Insofar as the detector plane DE and/or the diaphragm plane BE are slanted to the primary x-ray beam direction R, meaning slanted to the z-axis, the calculations are somewhat more complicated. The z-coordinates $z_{3a}$, $z_{3b}$, $z_{Pa}$, $z_{Pb}$ must then also each be calculated. For example, the coordinates $x_{B1}$, $y_{B1}$ of an arbitrary point in the diaphragm plane BE result from the coordinates $x_{D1}$, $y_{D1}$ of the corresponding point in the detector plane DE, i.e. in the subject localization exposure OA, according to the formulas:

$$x_{B1} = x_{D1} \cdot \frac{z_{B1}}{z_{D1}} \text{ and } y_{B1} = y_{D1} \cdot \frac{z_{B1}}{z_{D1}}$$

wherein $z_{B1}$ and $z_{D1}$ are the z-coordinates of the appertaining points.

FIG. 4 shows an alternative exemplary embodiment of a depth diaphragm 3' which has a total of 8 different diaphragm elements 3a, 3b, 3c, 3d, 3e, 3f, 3g, 3h. As in the exemplary embodiment according to FIG. 2, four of these diaphragm elements 3a, 3b, 3c, 3d can be moved toward the subject from the right, left, above or below. Moreover, the depth diaphragm 3' has four additional diaphragm elements 3e, 3f, 3g, 3h, offset by 45°, which can be correspondingly moved toward the diaphragm center point at 45° angles. As can be clearly seen from FIG. 4, a significantly better adaptation to the contour K of the exposure subject O is possible with such a diaphragm 3' having a number of diaphragm elements.

As the exemplary embodiments show, a very rapid and relatively precise adaptation of the diaphragm 3, 3' to the examination subject O is possible in a very simple manner with the aid of the inventive method, such that a subsequently x-ray exposure is generated under optimal conditions. Possible image artifacts due to deep radiation are reduced or largely prevented, Manual adjustment of the optimal diaphragm position is superfluous. Moreover, no elaborate special design of the detector or additional detector evaluation circuit is necessary for this purpose.

The designs shown in the figures and geometric arrangements are only exemplary embodiments. Arbitrary variations of these exemplary embodiments are thus possible in a wider scope without abandoning the framework of the invention. Although the invention was predominantly specified in the example of x-ray systems in the medical field, usage of the invention is not limited to this field, but the invention can also be used in scientific and/or industrially used x-ray systems.

Although modifications and changes may be suggested by those skilled in the art, it is the intention of the inventor to embody within the patent warranted hereon all changes and modifications as reasonably and properly come within the scope of his contribution to the art.

I claim:

1. A method for automatically adjusting a radiation diaphragm having a plurality of individually adjustable diaphragm elements, for subsequently obtaining a diagnostic radiation image, with a diagnostic radiation dose, of a subject, comprising the steps of:

irradiating the subject with a radiation dose substantially lower than said diagnostic radiation dose passing through said diaphragm with said diaphragm elements open to generate a non-diagnostic localization exposure of the subject from radiation striking a radiation detector, having a detector surface in a detector plane comprised of a plurality of pixels, said exposures being composed of image points respectively formed by combining a plurality of adjacent pixels into a group;

electronically, non-manually analyzing said localization exposure for determining only an exterior contour of the subject projected into said detector plane; and using said contour, automatically electronically calculating respective positions for the individual diaphragm elements at which the individual diaphragm elements substantially abut the exterior contour, and, before obtaining said diagnostic radiation image, automatically electronically moving the individual diaphragm elements to the respective calculated positions to substantially prevent direct irradiation of said radiation detector by radiation unattenuated by the subject when subsequently obtaining the diagnostic radiation image.

2. A method as claimed in claim 1 wherein said localization exposure contains at least one direct radiation region struck by radiation unattenuated by the subject, and a subject region struck by radiation attenuated by the subject, and wherein the step of analyzing said localization exposure comprises converting said localization exposure into a representation wherein said direct radiation region is designated with a first value and said subject region is designated with a second value.

3. A method as claimed in claim 1 wherein said radiation propagates in a primary beam direction, and wherein said diaphragm elements are disposed in a diaphragm plane, and wherein the step of calculating the respective positions of the individual diaphragm elements comprises calculating said positions using coordinates of at least one point on the contour of the subject in the localization exposure, a position of the detector plane relative to said primary beam direction, and a position of the diaphragm plane relative to said primary beam direction.

4. A method as claimed in claim 3 comprising calculating the respective positions using coordinates of said at least one point on the contour that, in said projection in the detector plane, form an outermost point of the contour in a direction of the diaphragm element whose position is being calculated.

5. A method as claimed in claim 3 wherein said diaphragm radiation image is subsequently obtained with radiation emitted from a focal spot of a radiation source, and wherein said radiation detector has a detector surface containing a plurality of detector elements disposed in rows and columns of a matrix, said detector surface being disposed perpendicularly to said primary beam direction, said method comprising the further steps of:

generating said localization exposure with radiation originating from said focal spot; and calculating the respective positions of the individual diaphragm elements using a coordinate system for defining said coordinates of said at least one point on the contour, said position of the detector plane, and said position of the diaphragm plane, having an origin at said focal spot and coordinate axes respectively proceeding in said primary beam direction and parallel to said rows and columns.

6. A method as claimed in claim 5 wherein said diaphragm plane is disposed perpendicularly to said primary beam direction, and wherein the step of calculating the respective positions of the individual diaphragm elements comprises, for each diaphragm element:

determining, as intermediate coordinates, coordinates of a point on the contour of the subject in the detector plane at which the diaphragm element would initially contact the contour as the diaphragm element is moved toward the contour; and multiplying said intermediate coordinates with a quotient of coordinates in said coordinate system representing the position of the diaphragm plane and coordinates in said coordinate system representing the position of the detector plane, for obtaining final coordinates for the diaphragm element.

7. A method for automatically adjusting a radiation diaphragm having a plurality of individual adjustable diaphragm elements, for subsequently obtaining a diagnostic radiation image, with a diagnostic radiation dose, of a subject, comprising the steps of:

irradiating the subject with a radiation dose substantially lower than said diagnostic radiation dose passing through said diaphragm with said diaphragm elements open to generate a non-diagnostic localization exposure of the subject from radiation striking a radiation detector, having a detector surface in a detector plane comprised of a plurality of pixels;

electronically, non-manually analyzing said localization exposure for determining only an exterior contour of the subject projected into said detector plane;

using said contour, automatically electronically calculating respective positions for the individual diaphragm elements at which the individual diaphragm elements substantially abut the exterior contour, and, before obtaining said diagnostic radiation image, automatically electronically moving the individual diaphragm elements to the respective calculated positions to substantially prevent direct irradiation of said radiation detector by radiation unattenuated by the subject when subsequently obtaining the diagnostic radiation image; and adding said localization exposure pixel-by-pixel to the subsequently obtained diagnostic radiation image.

8. A method as claimed in claim 7 wherein said localization exposure contains at least one direct radiation region struck by radiation unattenuated by the subject, and a subject region struck by radiation attenuated by the subject, and wherein the step of analyzing said localization exposure comprises converting said localization exposure into a representation wherein said direct radiation region is designated with a first value and said subject region is designated with a second value.

9. A method as claimed in claim 7 wherein said radiation propagates in a primary beam direction, and wherein said diaphragm elements are disposed in a diaphragm plane, and wherein the step of calculating the respective positions of the individual diaphragm elements comprises calculating said positions using coordinates of at least one point on the contour of the subject in the localization exposure, a position of the detector plane relative to said primary beam direction, and a position of the diaphragm plane relative to said primary beam direction.

10. A method as claimed in claim 9 comprising calculating the respective positions using coordinates of said at least one point on the contour that, in said projection in the detector plane, form an outermost point of the contour in a direction of the diaphragm element whose position is being calculated.

11. A method as claimed in claim 9 wherein said diaphragm radiation image is subsequently obtained with radiation emitted from a focal spot of a radiation source, and wherein said radiation detector has a detector surface containing a plurality of detector elements disposed in rows and columns of a matrix, said detector surface being disposed perpendicularly to said primary beam direction, said method comprising the further steps of:

generating said localization exposure with radiation originating from said focal spot; and calculating the respective positions of the individual diaphragm elements using a coordinate system for defining said coordinates of said at least one point on the contour, said position of the detector plane, and said position of the diaphragm plane, having an origin at said focal spot and coordinate axes respectively proceeding in said primary beam direction and parallel to said rows and columns.

12. A method as claimed in claim 11 wherein said diaphragm plane is disposed perpendicularly to said primary beam direction, and wherein the step of calculating the respective positions of the individual diaphragm elements comprises, for each diaphragm element:

determining, as intermediate coordinates, coordinates of a point on the contour of the subject in the detector plane at which the diaphragm element would initially contact the contour as the diaphragm element is moved toward the contour; and multiplying said intermediate coordinates with a quotient of coordinates in said coordinate system representing the position of the diaphragm plane and coordinates in said coordinate system representing the position of the detector plan, for obtaining final coordinates for the diaphragm element.

* * * * *